US012667248B2

(12) United States Patent
Robakiewicz et al.

(10) Patent No.: US 12,667,248 B2
(45) Date of Patent: Jun. 30, 2026

(54) TECHNIQUES FOR SUPPLYING FLUID TO AN ENDOSCOPE

(71) Applicant: BOSTON SCIENTIFIC SCIMED, INC., Maple Grove, MN (US)

(72) Inventors: Kurt Nicholas Robakiewicz, Upton, MA (US); Pauline Rosemary Limberg, Northborough, MA (US); Brian Luis, Worcester, MA (US); Ryan Vincent William Pollock, Leominster, MA (US); Ryan V. Wales, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1 day.

(21) Appl. No.: 18/816,412

(22) Filed: Aug. 27, 2024

(65) Prior Publication Data

US 2024/0415376 A1 Dec. 19, 2024

Related U.S. Application Data

(63) Continuation of application No. PCT/US2023/064573, filed on Mar. 16, 2023.
(Continued)

(51) Int. Cl.
*A61B 1/015* (2006.01)
(52) U.S. Cl.
CPC .................................... *A61B 1/015* (2013.01)
(58) Field of Classification Search
CPC ......... A61B 1/015; A61B 1/0125; A61B 1/05; A61B 1/045
See application file for complete search history.

(56) References Cited

U.S. PATENT DOCUMENTS

2006/0106285 A1* 5/2006 Boulais .................. A61B 1/128
600/156
2007/0249993 A1 10/2007 Mollstam et al.
(Continued)

FOREIGN PATENT DOCUMENTS

GB 2610814 A * 3/2023 ......... A61B 1/00124
JP H06189957 A 7/1994
(Continued)

OTHER PUBLICATIONS

International Search Report and Written Opinion for International Application No. PCT/US2023/064573, dated Jun. 9, 2023. (12 Pages).

*Primary Examiner* — Kevin T Truong
*Assistant Examiner* — Diana Jones
(74) *Attorney, Agent, or Firm* — Seager, Tufte & Wickhem, LLP

(57) ABSTRACT

Various embodiments described hereby may separate one or more functionalities/components provided via the tower in order to alleviate the physical barrier created by the umbilicus and reduce the need of the umbilicus to connect to the tower. For example, the liquid source may be worn by the user (e.g., physician) or the liquid source may modularly attach to the endoscope, such as to the handle of the endoscope. Accordingly, several embodiments described hereby may improve user experience such as by giving the user greater freedom of movement without sacrificing functionality. Some embodiments provide a source and means of using water without requiring the umbilicus to physically attach to the tower, improving range and ease of motion for a user by removing the need to navigate about a water connector.

16 Claims, 9 Drawing Sheets

Related U.S. Application Data

(60) Provisional application No. 63/320,970, filed on Mar. 17, 2022.

(56) References Cited

U.S. PATENT DOCUMENTS

| | | | | |
|---|---|---|---|---|
| 2008/0207028 A1* | 8/2008 | Schutz | ................. | H01R 13/005 |
| | | | | 439/191 |
| 2015/0057500 A1* | 2/2015 | Salman | .............. | A61B 1/00006 |
| | | | | 600/132 |
| 2016/0073867 A1 | 3/2016 | Ramsey | | |

FOREIGN PATENT DOCUMENTS

| | | | | | |
|---|---|---|---|---|---|
| JP | 2003070730 | A | 3/2003 | | |
| JP | 2003070731 | A | 3/2003 | | |
| JP | 2004198651 | A | 7/2004 | | |
| JP | 2004337188 | A | 12/2004 | | |
| JP | 2006288881 | A | 10/2006 | | |
| WO | WO-2020079417 | A1 * | 4/2020 | ............. | A61B 1/126 |

* cited by examiner

TECHNIQUES FOR SUPPLYING FLUID TO AN ENDOSCOPE

CROSS REFERENCE TO RELATED APPLICATIONS

This application claims priority to PCT/US2023/064573, filed Mar. 16, 2023, which claims the benefit of priority of U.S. Provisional Application No. 63/320,970 filed Mar. 17, 2022, the entire disclosures of which are hereby incorporated by reference.

FIELD

The present disclosure relates generally to the field of medical devices. In particular, the present disclosure relates to devices, systems, and methods to supply fluid to an endoscope.

BACKGROUND

Conventionally, endoscope devices have been widely used for performing diagnostic and/or therapeutic treatments. Such endoscope devices sometimes include a fluid capability, or the like, configured to feed fluid to the end of the endoscope for insufflating the inside of the patient at the target site. Lens wash provides a liquid such as sterilized water at relatively high pressure to spray across and clear the camera lens of debris. The water source for lens wash and irrigation typically has included one or more fluid reservoirs with tubing and cap assemblies that creates the plumbing circuit in connection with the endoscope channels and valving via an umbilicus to accomplish the gas and water functions described. Such tubing and cap assemblies are available in various configurations, which typically involve a water bottle, a cap fitted for the specific bottle, and an array of tubing that is extendable through openings in the cap. The tubing typically is arranged to accommodate a specific configuration of endoscope fittings and valving.

It is with these considerations in mind that the improvements of the present disclosure may be useful.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one aspect, the present disclosure relates to an apparatus including an umbilicus, an elongate member, and a handle fixedly coupled to the umbilicus and the elongate member. The elongate member may include at least one lumen. The handle may comprise a control interface and a supply port. The control interface may be operable to control fluid communication between the supply port and the at least one lumen. The handle may include at least one electrical connection to the elongate member. The liquid source may include an adapter and a reservoir removably coupled to the adapter and the adapter removably coupled to the handle via the supply port.

In various embodiments, the liquid source comprises a pump to cause a fluid to flow from the reservoir into the at least one lumen in response to operation of the control interface. In various such embodiments, the pump comprises a peristaltic pump. In some embodiments, the liquid source comprises a compressed gas canister to cause a fluid to flow from the reservoir into the at least one lumen in response to operation of the control interface. In many embodiments, the liquid source is disposed in a wearable device. In many such embodiments, the wearable device comprises a backpack. In some such embodiments, the wearable device includes a power source configured to operate the liquid source. In several embodiments, the adapter includes threads that the reservoir screws into. In various embodiments, the supply port includes threads that the adapter screws into. In some embodiments, the control interface comprises an air/water valve. Many embodiments include a sensor communicatively coupled to the liquid source, the sensor configured to indicate a position of the control interface and the liquid source comprising a pump configured to cause a fluid to flow from the reservoir into the at least one lumen in response to the position of the control interface indicated by the sensor. In several embodiments, the liquid source comprises a condenser configured to extract liquid from an atmosphere and dispense the liquid into the reservoir. Various embodiments include a gas source configured to pressurize the reservoir in response to operation of the control interface. Some embodiments comprise tower including a video processor wherein the umbilicus couples the handle to the tower and the video processor is coupled to the at least one electrical connection in the handle via an umbilicus. In some such embodiments, the tower includes a gas source configured to pressurize the reservoir in response to operation of the control interface.

In another aspect, the present disclosure relates to an apparatus comprising a wearable device, an elongate member, a handle, and a liquid source. The elongate member may include at least one lumen. The handle may be fixedly coupled to the wearable device and the elongate member. The handle may include a control interface and a supply port. The control interface may be operable to control fluid communication between the supply port and the at least one lumen. The handle may include at least one electrical connection between the wearable device and the elongate member. The liquid source may include an adapter and a reservoir removably coupled to the adapter and the adapter removably coupled to the handle via the supply port.

In various embodiments, the wearable device comprises a gas source to cause a fluid to flow from the reservoir into the at least one lumen in response to operation of the control interface. In some embodiments, the wearable device comprises a wireless transceiver configured to wirelessly couple a video processor to the elongate member via the at least one electrical connection. Some such embodiments include a tower comprising the video processor and a wireless transceiver configured to couple with the wireless transceiver in the wearable device. In many embodiments, the wearable device comprises a condenser configured to extract liquid from an atmosphere and dispense the liquid into the reservoir.

BRIEF DESCRIPTION OF THE DRAWINGS

The accompanying drawings, which are incorporated in and constitute a part of this specification, illustrate various exemplary embodiments and together with the description serve to explain the principles of the present disclosure.

DETAILED DESCRIPTION

Figure 1:
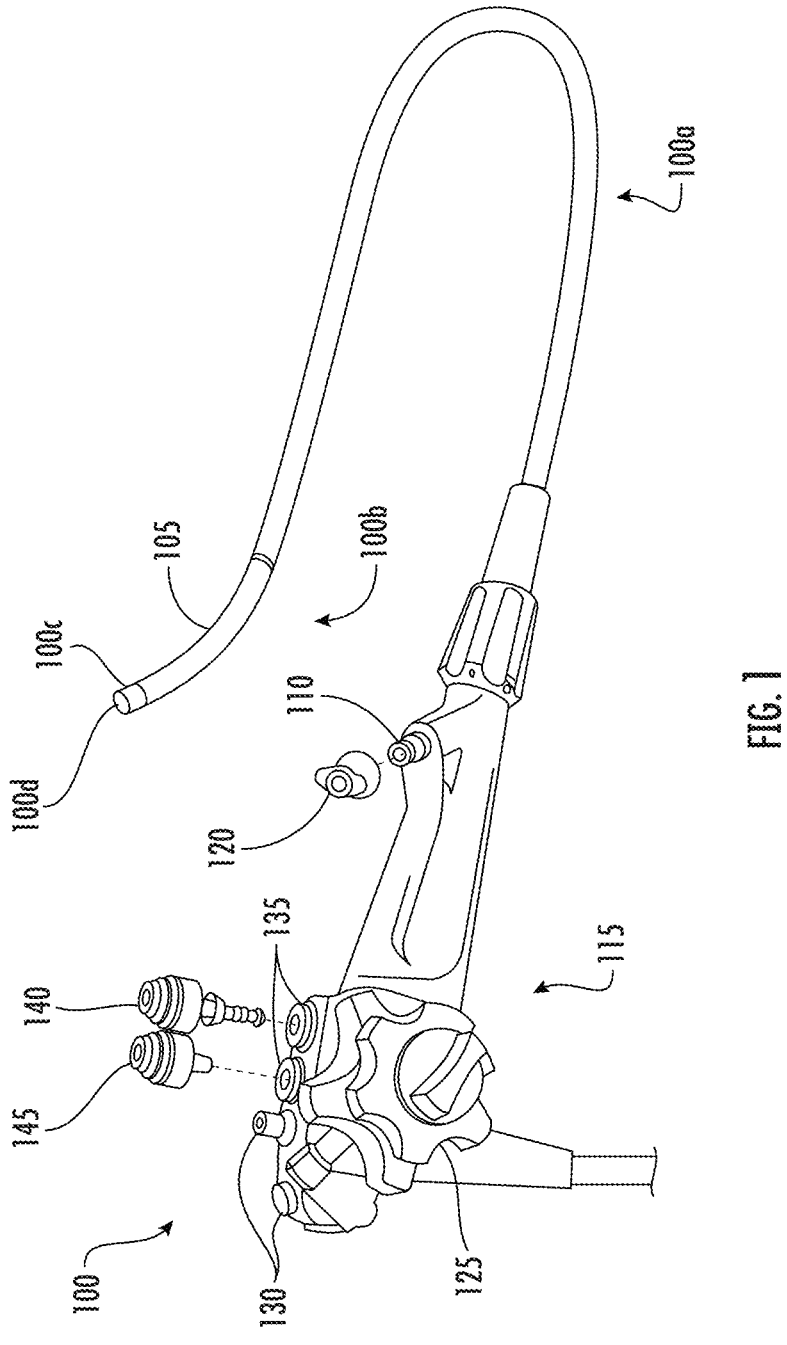
FIG. 1 illustrates an aspect of the subject matter in accordance with one embodiment.

Several procedures may be performed by physicians through the use of an endoscope. Frequently during the procedures, a physician may be required to move their body relative to the endoscope handle to perform certain procedure-critical motions inside the human body. In these cases, the physician can be limited by the body of the umbilicus, which houses the connection between the scope and the tower. One of the important functions supplied by the scope tower is having a liquid source (e.g., water). This liquid source may serve the function of supplying water to clean debris from the lens to improve visualization or to wash away debris seen in the body. For some procedures, such as endoscopic retrograde cholangiopancreatography (ERCP), endoscopic lumbar sympathectomy (ELS), endoscopic mucosal resection (EMR), etcetera, it can be cumbersome for a physician to continuously attempt to contort their body to avoid the umbilicus while performing the procedures. Accordingly, the umbilicus can act as a physical barrier which prevents full freedom of motion for the individual using the endoscope. This can limit the range of motion and may require the physician to move themselves into uncomfortable positions to adequately perform a procedure.

In order to alleviate the physical barrier created by the umbilicus and reduce the need of the umbilicus to connect to the tower, various embodiments described hereby may separate one or more functionalities/components provided via the tower. For example, the liquid source may be worn by the user (e.g., physician) or the liquid source may modularly attach to the endoscope, such as to the handle of the endoscope. Accordingly, several embodiments described hereby may improve user experience such as by giving the user greater freedom of movement without sacrificing functionality. Some embodiments provide a source and means of using water without requiring the umbilicus to physically attach to the tower, improving range and case of motion for a user by removing the need to navigate about a water connector. Various embodiments include no physical connections between the scope and tower, removing the need to navigate about any connections between the scope and the tower.

This disclosure is described with reference to an exemplary medical system that may be used in endoscopic medical procedures. However, it should be noted that reference to this particular procedure is provided only for convenience and not intended to limit the disclosure. A person of ordinary skill in the art would recognize that the concepts under lying the disclosed devices and related methods of use may be utilized in any suitable procedure, medical or otherwise. This disclosure may be understood with reference to the following description and the appended drawings, wherein like elements are referred to with the same reference numerals.

As used herein, the term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately," and "substantially" indicate a range of values within +/−10% of a stated or implied value. Additionally, terms that indicate the geometric shape of a component/surface refer to exact and approximate shapes.

Although embodiments of the present disclosure are described with specific reference to a tubing assembly for use in distributing liquid from a reservoir (e.g., container, bottle, or the like) and one or more gases from different sources, it should be appreciated that such embodiments may be used to supply liquid and/or gas to and/or from an endoscope, for a variety of different purposes, including, for example to facilitate insufflation of a patient, lens washing, and/or to irrigate the working end of an endoscope in a patient to aid in flushing/rinsing the body lumen and/or to clear debris from the field of view of the endoscope in the body lumen, during an endoscopic procedure. Use of "lens wash" refers to liquid (e.g., water) being flowed, typically at a higher flow rate and pressure compared to irrigation, to a nozzle or other opening at a distal end of an endoscope for the purpose of washing or otherwise clearing or cleaning the lens covering an imaging or light source at the distal end of the endoscope.

Although the present disclosure includes description of a bottle and tube set (e.g., a tubing assembly) suitable for use with an endoscope system to supply liquids to an endoscope, the devices, systems, and methods herein could be implemented in other medical systems requiring fluid delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Figure 2:
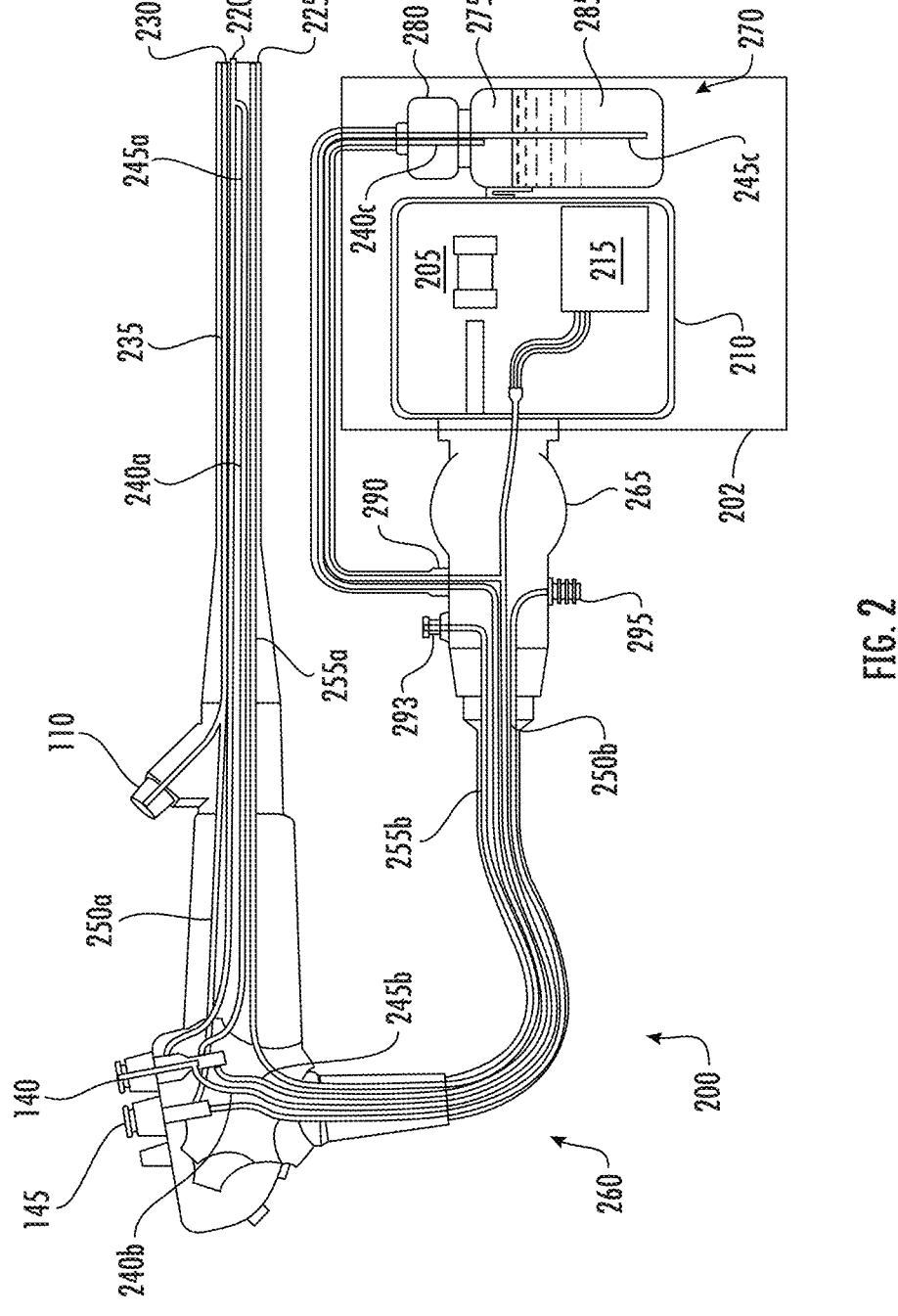
FIG. 2 illustrates an aspect of the subject matter in accordance with one embodiment.

FIGS. 1 and 2, and the corresponding description, illustrate a general case of how fluids may be provided to the distal end of an endoscope. However, in various embodiments described hereby, one or more components in the tower 202 may be relocated, such as to a wearable, or portable, device or integrated into the handle 115, in order to improve usability of the endoscope 100. For example, relocating one or more components from the tower may reduce or eliminate the physical barrier to a user created by the umbilicus 260. In various embodiments, reducing the physical barrier to a user created by the umbilicus 260 may include making the umbilicus 260 more flexible and/or narrower, such as by removing one or more fluid channels from passing through the umbilicus. In some embodiments, all physical barriers created by the umbilicus 260 may be removed, such as by remove all connections between the handle 115 and the tower 202. Embodiments are not limited in this context.

With reference to FIGS. 1-2, an exemplary endoscope 100 and system 200 is depicted that may comprise an elongate member 100a that is insertable into a patient. A light source 205 feeds illumination light to a distal portion 100b of the endoscope 100, which may house an imager (e.g., CCD or CMOS imager) (not shown). The light source 205 (e.g., lamp) is housed in a tower 202 comprising a video processing unit 210, or video processor, that processes signals that are input from the imager and outputs processed video signals to a video monitor (not shown) for viewing. In some embodiments, tower 202 also serves as a component of an air/water feed circuit by housing a pressurizing pump 215 (or gas source), such as an air feed pump, in the unit. In illustrated embodiment, the video processing unit 210 of the tower 202 houses the pressurizing pump 215 and the light source 205.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation liquid to the treatment area of the patient. Illumination windows (not shown) that convey illumination light to the treatment area, and an opening 230 to a working channel 235 extending along the shaft 100a for passing tools to the treatment area, also may be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress. In some embodiments, channel opening 110 may include a luer connection. In some such embodiments, biopsy valve 120 may couple to the channel opening 110 via the luer connection. In various embodiments, biopsy valve 120 may include, or refer to, one or more of a biopsy cap, biopsy port cap, and biopsy port seal. In one embodiment, the biopsy valve 120 may include a polymer cap.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle is provided with dual valve wells 135 that receive a gas/lens wash valve 140 (or air/water valve) for operating an insufflating gas and lens water feed operation. A gas supply line 240a and a lens wash (e.g., liquid) supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the tower 202, via a flexible umbilicus 260 and connector portion 265 extending therebetween. The flexible umbilicus 260 has a gas (e.g., air or $CO_2$) feed line 240b, a lens wash feed line 245b, a suction feed line 250b, an irrigation feed line 255b, a light guide (not shown), and an electrical signal cable (not shown). The connector portion 265 when plugged into the video processing unit 210 connects the light source 205 in the video processing unit with the light guide. The light guide runs along the umbilicus 260 and the length of the endoscope shaft 100a to transmit light to the distal tip 100c of the endoscope 100. The connector portion 265 when plugged into the tower 202 also connects the air pump 215 to the gas feed line 240b in the umbilicus 260.

A liquid reservoir 270 (e.g., water bottle or other type of container for retaining a fluid) is fluidly connected to the endoscope 100 through the connector portion 265 and the umbilical 260. A portion of gas supply tubing 240c passes from one end positioned in an air gap 275 between the top 280 (e.g., bottle cap or closure device) of the reservoir 270 and the remaining water 285 in the reservoir to a detachable gas/lens wash connection 290 on the outside of the connector portion 265. The gas feed line 240b from the umbilicus 260 branches in the connector portion 265 to fluidly communicate with the gas supply tubing 240c at the detachable gas/lens wash connection 290, as well as the air pump 215. A portion of lens wash tubing 245c, with one end positioned at the bottom of the reservoir 270, passes through the top 280 of the reservoir to the same detachable connection 290 as the gas supply tubing 240c on the connector portion 265. In other embodiments, the connections may be separate and/or separated from each other, such as located in a wearable, or portable, device or on the handle 115. The connector portion 265 also has a detachable irrigation connection 293 for irrigation supply tubing (not shown) running from a source of irrigation liquid (not shown) to the irrigation feed line 255b in the umbilicus 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same liquid reservoir. The connector portion 265 may also include a detachable suction connection 295 for suction feed line 250b and suction supply line 250a fluidly connecting a vacuum source (e.g., hospital house suction) (not shown) to the umbilicus 260 and endoscope 100.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the tower 202 is flowed through the connection portion 265 and branched to the gas/water valve 140 on the operating handle 115 through the gas feed line 240b in the umbilicus 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilicus 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate compared to lens wash is typically required for irrigation water, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump 255c is connected to the irrigation feed line 255b in the umbilicus 260 and the irrigation supply line 255a of endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilicus, and down the irrigation supply line in the shaft 100a of the endoscope to the distal tip 100c. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245c, may be placed in the path of the irrigation supply tubing to help prevent back-flow into the reservoir after water has passed the valve.

Figure 3:
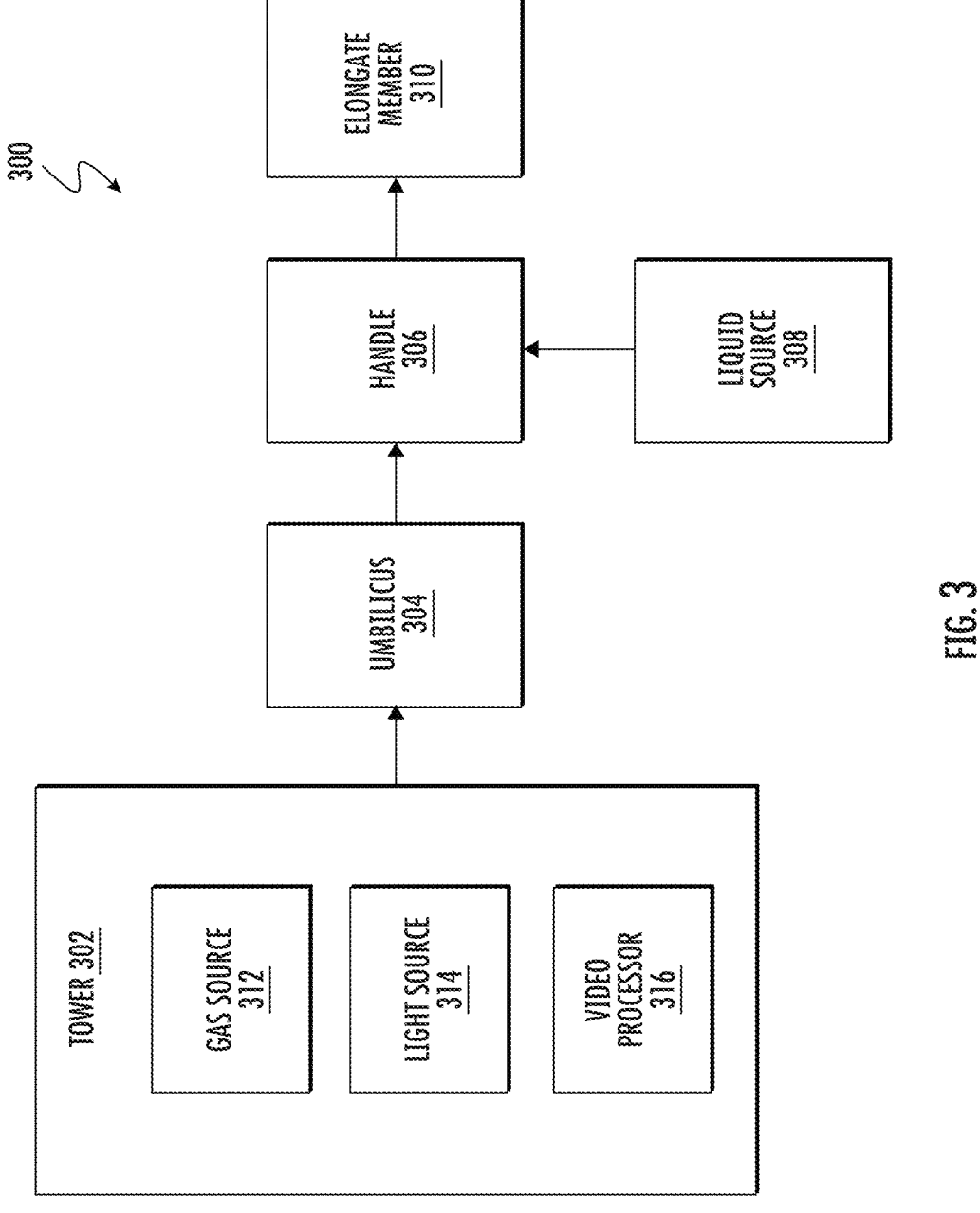
FIG. 3 illustrates an aspect of the subject matter in accordance with one embodiment.

FIG. 3 illustrates a block diagram of an endoscopic system 300 with a liquid source 308 that directly couples to a handle 306 according to one or more embodiments described hereby. In the illustrated embodiment, endoscopic system 300 includes a tower 302, an umbilicus 304, a handle 306, liquid source 308, and elongate member 310. The tower 302 may include a gas source 312, a light source 314, and a video processor 316. By directly coupling the liquid source 308 to the handle 306, the umbilicus 304 of endoscopic system 300 has greater flexibility when compared to the umbilicus 260 of endoscopic system 200. In many embodiments, the handle 306 may include at least one electrical connection to the elongate member 310, such as one or more electrical connections between the umbilicus 304 and the elongate member 310. It will be appreciated that additional or alternative components may be included in, or excluded from, endoscopic system 300 without departing from the scope of this disclosure. For example, gas source 312 may be integrated into the liquid source 308. Embodiments are not limited in this context.

In various embodiments, the liquid source 308 may provide lens wash and/or irrigation to the elongate member 310 based on operation of control interfaces on handle 306. In various embodiments, the liquid source 308 may removably couple to the handle 306 and be readily replaced with additional liquid sources. In one or more embodiments, liquid source 308 may include a means for causing liquid to flow through the handle and into the elongate member 310, such as by pressurizing the liquid. In other embodiments, the gas source 312 may be utilized to pressurize liquid in the liquid source 308 and cause the liquid to flow through the handle and into the elongate member 310. It will be appreciated that reference to tubing, lines, channels, and/or components being in fluid communication implies that a lumen is included therein and/or therebetween.

In some embodiments, the handle 306 may include a supply port that the liquid source 308 couples to. The liquid source 308 may include an adapter and a reservoir. The adapter may couple to the supply port of the handle 306 and the reservoir. In some embodiments, the adapter may include a quick disconnect such that the reservoir can be readily replaced. In various embodiments, the liquid source 308 may include a diaphragm or a bladder that is utilized to force liquid out of the reservoir. For example, the reservoir may be collapsible and the liquid source 308 may include a compressed gas canister that forces liquid out of the reservoir, such as by filling a bladder in the liquid reservoir. In another example, the adapter of the handle 306 may be configured to couple with a gas source and introduce gas into the reservoir to force liquid out.

In various embodiments, the handle 306 may include a sensor that can determine a position of a control interface on the handle. In some such embodiments, the liquid source 308 may provide liquid to the elongate member 310 based on data provided by the sensor. Many embodiments may include one or more sensors communicatively coupled with a liquid and/or gas source to control operation of the liquid and/or gas source. In many embodiments, one or more control interfaces described hereby may include suction valve 145 and/or gas/lens wash valve 140. In various embodiments, light source 314 may be the same or similar to light source 205. In one embodiment, light source 314 may provide illumination to a distal end of the elongate member 310 via an optical fiber. The video processor 316 may be the same or similar to video processing unit 210.

Figure 4A:
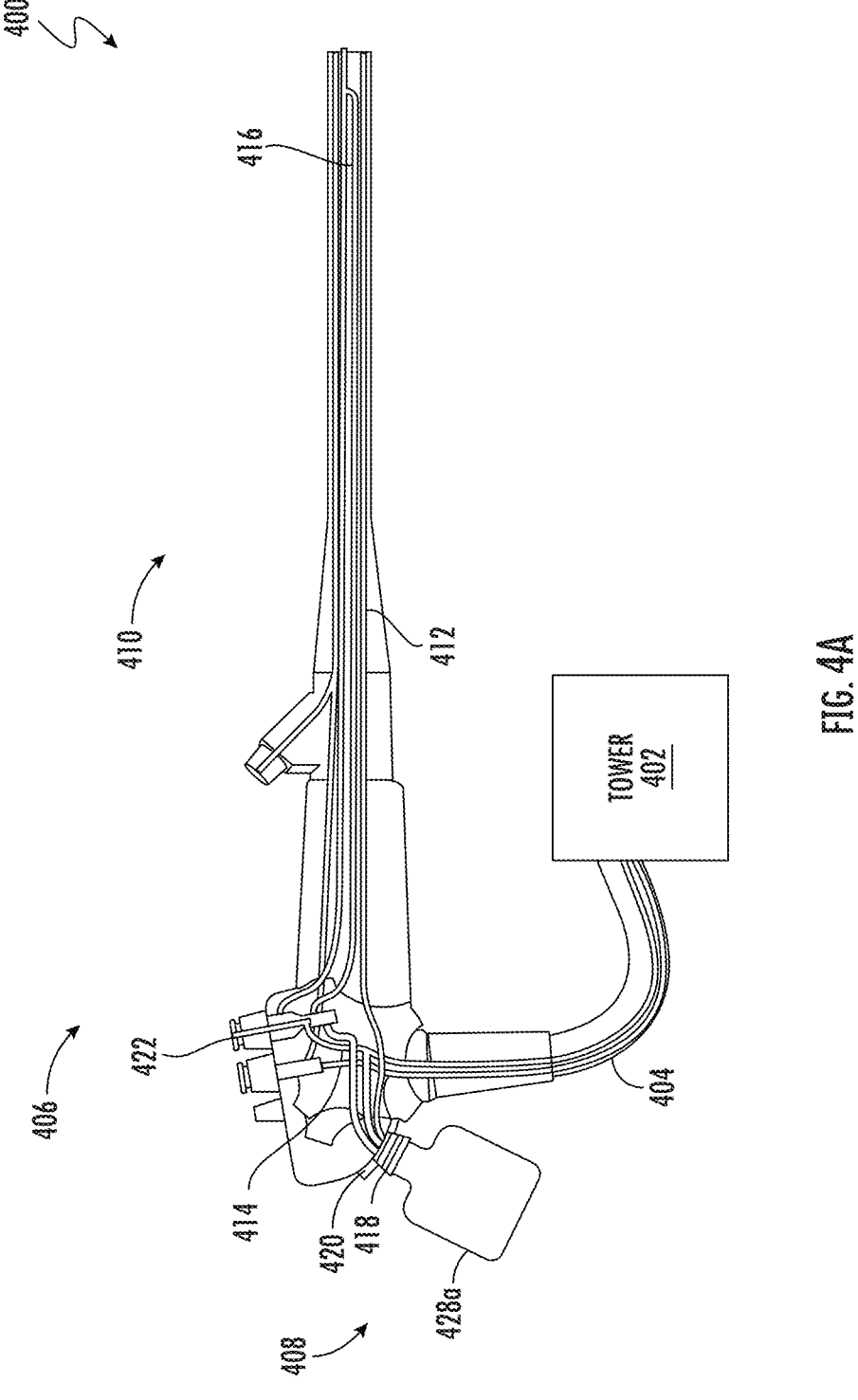
FIG. 4A illustrates an aspect of the subject matter in accordance with one embodiment.
Figure 4B:
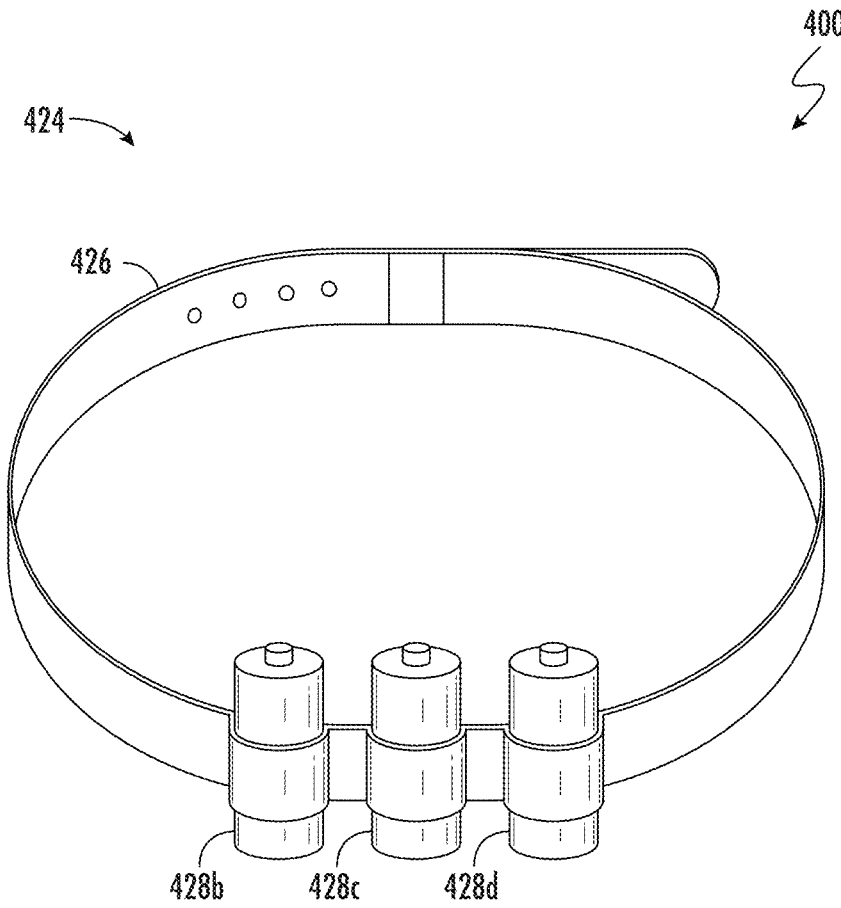
FIG. 4B illustrates an aspect of the subject matter in accordance with one embodiment.

FIGS. 4A and 4B illustrate an exemplary embodiment of an endoscopic system 400 with a liquid source 408 that directly couples to a handle 406 according to one or more embodiments described hereby. Endoscopic system 400 includes a tower 402, an umbilicus 404, a handle 406, a liquid source 408, an elongate member 410, and a wearable device 424. As shown in FIG. 4A, the tower 402 is coupled to the handle 406 via the umbilicus 404. The handle 406 may include a supply port 420, a control interface 422, and a portion of an irrigation supply line 412. As shown in FIG. 4B, the wearable device 424 may include a belt 426 with a plurality of replacement reservoirs 428b, 428c, 428d. In various embodiments, reservoir 428a may be exchangeable with reservoirs 428b, 428c, 428d. It will be appreciated that additional or alternative components may be included in, or excluded from, endoscopic system 400 without departing from the scope of this disclosure. Embodiments are not limited in this context.

The control interface 422 may be used to control fluid communication between the irrigation supply line 412 and/or the lens wash supply line 416 and the supply port 420. In various embodiments, the control interface 422 may comprise an air/water valve. In some embodiments, the handle 406 may include a sensor that is utilized by the liquid source 408 to determine whether to provide liquid to the irrigation supply line 412 or the lens wash supply line 416 based on the position of the control interface 422. The liquid source 408 may include an adapter 418 and a reservoir 428a. The adapter 418 may removably, or fixedly, couple to the supply port 420 and facilitate fluid communication between the reservoir and the supply port 420. In various embodiments, the supply port 420 may include threads that the adapter 418 screws into. Additionally, or alternatively, the adapter 418 may include threads that the reservoir screws into. In the illustrated embodiment, the umbilicus 404 includes a gas feed line 414, but umbilicus 404 does not include an irrigation feed line or lens wash feed line. Instead, liquid for lens wash and/or irrigation is supplied via the liquid source 408 coupled to the handle 406. In the illustrated embodiment, the gas feed line 414 includes a 'T' junction that allows it to be used to pressurize the reservoir to force liquid out of the liquid source 408 toward the elongate member 410.

One of the key components to using liquid (e.g., water) in an endoscopic procedure is having a source from which the scope draws water. The endoscopic system 400 may enable the physician to have a set of reservoirs 428a, 428b, 428c, 428d (or reservoirs 428) that can quickly be switched out. The reservoirs 428 may be single-use or reusable. In some embodiments, the reservoirs 428 may include water bottles or packets. The reservoirs 428 may attach either directly to the scope or through an additional device (e.g., adapter 418) that acts as a medium between the reservoirs and the irrigation supply line 412 and the lens wash supply line 416.

Another key component to using liquid (e.g., water) in an endoscopic procedure is being able to pressurize the water to force it down the water channel (e.g., irrigation supply line 412 and/or lens wash supply line 416) of the scope. In some embodiments, the liquid source 408 includes a diaphragm or bladder that squeezes liquid in the reservoir and forces it out. In various embodiments, the squeezing force may be achieved through various means, such as pistons, hydraulics, air expansion chamber, foot pedal, or gears with a lead screw. Gas sources may operate based on similar squeezing forces. In the illustrated embodiment, a pressure source is provided from the tower 402 via umbilicus 404 and gas feed line 414. For example, fluid may be forced out of the reservoirs 428a in a manner similar to the pressurizing pump 215 of endoscopic system 200.

Figure 5:
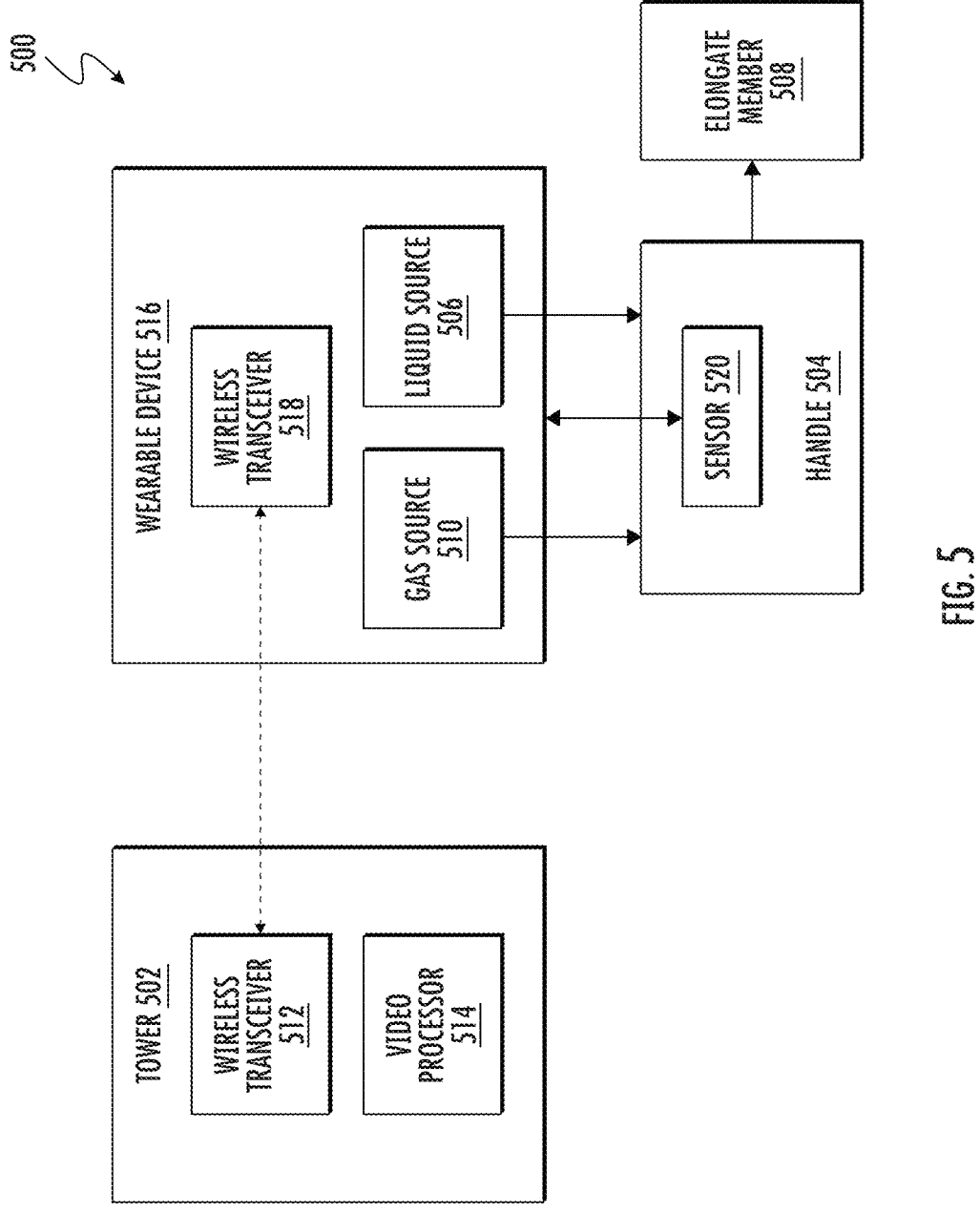
FIG. 5 illustrates an aspect of the subject matter in accordance with one embodiment.

FIG. 5 illustrates a block diagram of an endoscopic system 500 with a wearable device 516 that incorporates a gas source 510 and a liquid source 506 according to one or more embodiments described hereby. The endoscopic system 500 excludes a physical connection between the tower 502 and the handle 504. Instead, wearable device 516 includes the gas source 510 and the liquid source 506. Additionally, tower 502 and wearable device 516 include wireless transceivers 512, 518 to facilitate communication between the video processor 514 and the elongate member 508 via at least one electrical connection in the handle 504. Accordingly, in various embodiments, elongate member 508 may include a sensor, such as a video camera. In some embodiments, wearable device 516, or handle 504, may include a light source coupled to elongate member 508, such as in a similar manner as with respect to light source 314. In one embodiment, the light source may be coupled to an optical fiber that extends to a distal end of the elongate member 310. Embodiments are not limited in this context.

Handle 504 includes sensor 520 that is utilized to determine a position of one or more control interfaces and activate one or more of the gas source 510 and the liquid source 506 such as for providing gas, lens wash, and/or irrigation to elongate member 508. In several embodiments, the handle 504 include one or more electrical connections to the elongate member 508. In some embodiments, the liquid source 506 may provide liquid at a first flow rate for lens wash and a second flow rate for irrigation. In some such embodiments, the first flow rate may be lower than the second flow rate. It will be appreciated that additional or alternative components may be included in, or excluded from, endoscopic system 500 without departing from the scope of this disclosure. For example, sensor 520 may be excluded from handle 504. The video processor 514 may be the same or similar to video processing unit 210.

Figure 6:
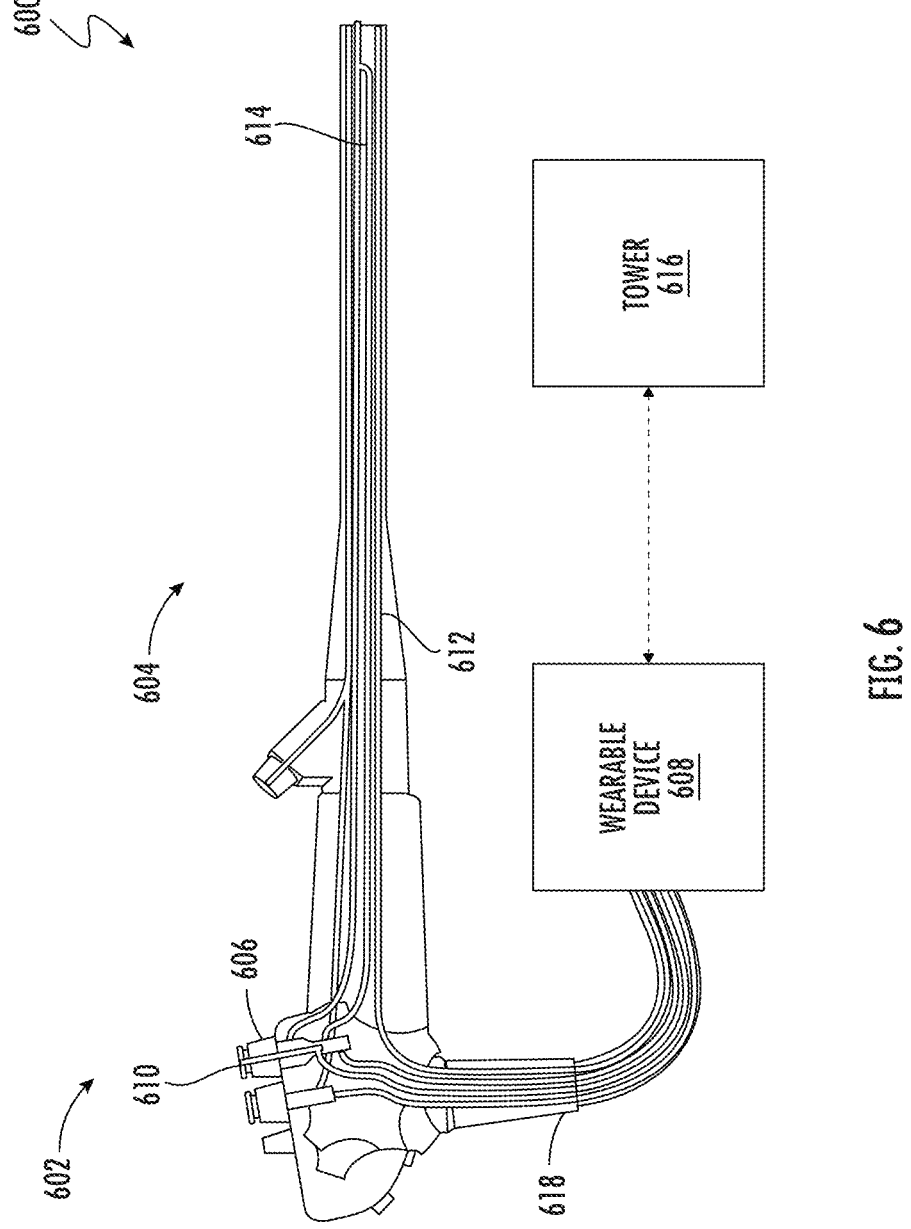
FIG. 6 illustrates an aspect of the subject matter in accordance with one embodiment.

FIG. 6 illustrates an exemplary embodiment of an endoscopic system 600 with a wearable device 608 that wirelessly connects to a tower 616 according to one or more embodiments described hereby. The endoscopic system 600 includes a handle 602, an elongate member 604, wearable device 608, and tower 616. The handle 602 may be coupled to the wearable device 608 via a supply port 618. In some embodiments, the connection between the handle 608 and the wearable device 608 may be referred to as an umbilicus. In the illustrated embodiment, the handle 602 includes a control interface 610 with a sensor 606. In many embodiments, the control interface 610 comprises an air/water valve. In various embodiments, the sensor 606 is utilized by the wearable device 608 to determine a position of control interface 610 and based on the position of the control interface 610 the wearable device 608 may provide one or more of air, lens wash, and irrigation to the elongate member 604. In one embodiment, multiple control interfaces may be included along with multiple sensors for controlling the provision of one or more of air, lens wash, and irrigation to the elongate member 604. For example, a user may manually select between whether irrigation or lens wash is provided. In one such example, irrigation may be provided unless the control interface 610 is depressed. In some embodiments, the speed of a pump may be controlled based on the position of the control interface 610. In some such embodiments, variable flow rates for lens wash and/or irrigation may be provided based on the position of the control interface 610. It will be appreciated that additional or alternative components may be included in, or excluded from, endoscopic system 600 without departing from the scope of this disclosure. For example, sensor 606 may be excluded from handle 602. Embodiments are not limited in this context.

Figure 7A:
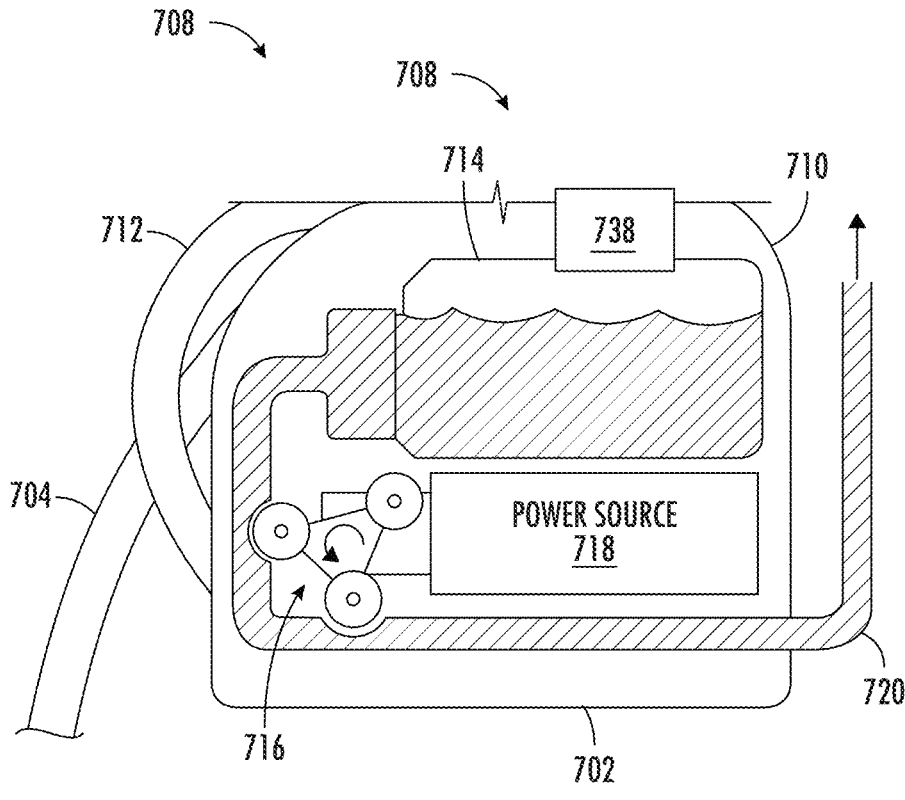
FIG. 7A illustrates an aspect of the subject matter in accordance with one embodiment.
Figure 7B:
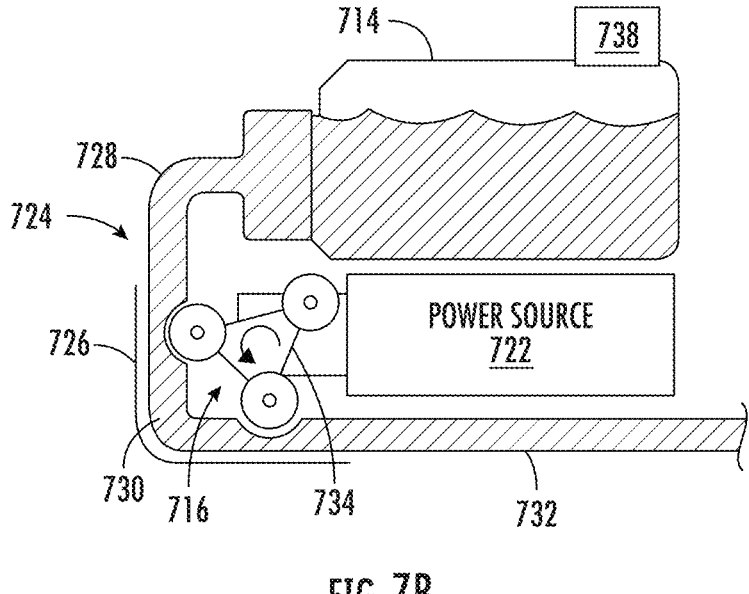
FIG. 7B illustrates an aspect of the subject matter in accordance with one embodiment.
Figure 7C:
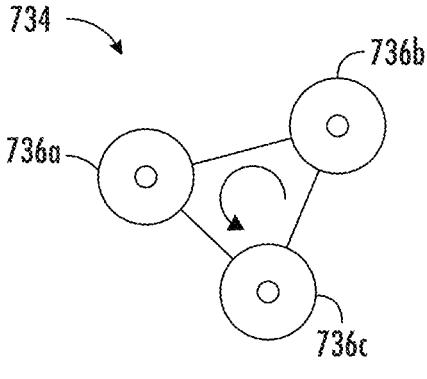
FIG. 7C illustrates an aspect of the subject matter in accordance with one embodiment.

FIGS. 7A-7C illustrate an exemplary embodiment of a wearable device 706 including a liquid source 708 according to one or more embodiment described hereby. In the illustrated embodiment, the wearable device 706 includes a backpack 710 with a strap 712 that is coupled to a user 702 with an arm 704. The liquid source 708 includes reservoir 714, pump 716, power source 718, supply tubing 720, and condenser 738. It will be appreciated that additional or alternative components may be included in, or excluded from, wearable device 706 without departing from the scope of this disclosure. For example, a gas source may be integrated into wearable device 706. In another example, the condenser 738 may be excluded from the liquid source 708. Embodiments are not limited in this context.

Referring to FIG. 7A, in many embodiments, the power source 718 may be utilized to operate the pump 716. In various embodiments, the power source 718 may comprise batteries. In the illustrated embodiment, pump 716 comprises a peristaltic pump. In other embodiments, one or more of a rotary lobe pump, a progressive cavity pump, a rotary gear pump, a piston pump, a diaphragm pump, a screw pump, a gear pump, and a hydraulic pump may be utilized. Similarly, one or more gas sources describe hereby may include one or more of the above mentioned pump types to cause gases to flow. In various embodiments, the supply tubing 720 may couple with the handle of an endoscopic system, such as via a supply port, to provide liquid to the endoscopic system. The condenser 738 may be utilized to continuously refill the reservoir 714 by extracting water from the ambient atmosphere. In the illustrated embodiment, the wearable device 706 includes a backpack. In other embodiments, the wearable device 706 may include a hip belt, such as a front-worn or back-worn fanny pack. In one embodiments, the wearable device 706 may include a backpack combined with a hip belt. More generally, in some embodiments, a wearable device may comprise a portable device that is not necessarily worn by a user without departing from the scope of this disclosure. For example, one or more of a liquid source, a gas source, and a wireless transceiver may be carried by a user.

Referring to FIG. 7B, the supply tubing 720 may include an upstream tubing section 728, a pump tubing section 730, and a downstream tubing section 732. The upstream tubing section 728 may provide fluid communication between the reservoir 714 and the pump 716. The pump 716 may include a rotor 734 and a pump wall 726. As seen in FIG. 7C, the rotor 734 may have a triangular shape and include a plurality of rollers 736a, 736b, 736c. In operation the rotor 734 may rotate causing the rollers 736a, 736b, 736c to compress portions of the pump tubing section 730 against the pump wall 726 to force liquid from the reservoir 714 into the downstream tubing section 732. In various embodiments, the speed at which the rotor 734 turns may be based upon the position of a control interface. As previously mentioned, in many embodiments, the position of the control interface may be determined based on a sensor.

In various embodiments, the upstream tubing section 728 may removably couple to the reservoir 714, such as via a cap. In the illustrated embodiment, the pump wall 726 includes an approximately ninety-degree bend to enable the upstream tubing section 728 and the downstream tubing section 732 to be oriented at approximately ninety degrees with respect to each other. In other embodiments, the pump wall 726 may include a second approximately ninety-degree bend to create a 'U' shape to enable the upstream tubing section 728 and the downstream tubing section 732 to be oriented at approximately 180 degrees with respect to each other.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of approximately 9.7 mm. The lens wash supply tubing may have an inner diameter of approximately 5 mm and an outer diameter of approximately 8 mm. The gas supply tubing may have an inner diameter of approximately 2 mm and an outer diameter of approximately 3.5 mm. The alternative gas supply tubing may have an inner diameter of approximately 5 mm and an outer diameter of approximately 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed:

1. An apparatus, comprising:
an elongate member comprising at least one lumen;
a handle fixedly coupled to the elongate member, the handle comprising a control interface and a supply port, the control interface operable to control fluid communication between the supply port and the at least one lumen, wherein the handle includes at least one electrical connection to the elongate member; and
a liquid source comprising an adapter and a reservoir removably coupled to the adapter and the adapter removably coupled to the handle via the supply port, wherein the liquid source is disposed in a wearable device.

2. The apparatus of claim 1, wherein the liquid source comprises a pump to cause a fluid to flow from the reservoir into the at least one lumen in response to operation of the control interface.

3. The apparatus of claim 2, wherein the pump comprises a peristaltic pump.

4. The apparatus of claim 1, wherein the liquid source comprises a compressed gas canister to cause a fluid to flow from the reservoir into the at least one lumen in response to operation of the control interface.

5. The apparatus of claim 1, wherein the wearable device comprises a backpack.

6. The apparatus of claim 1, wherein the wearable device includes a power source configured to operate the liquid source.

7. The apparatus of claim 1, wherein the adapter includes threads that the reservoir screws into.

8. The apparatus of claim 1, wherein the supply port includes threads that the adapter screws into.

9. The apparatus of claim 1, wherein the control interface comprises an air/water valve.

10. The apparatus of claim 1, comprising a sensor communicatively coupled to the liquid source, the sensor configured to indicate a position of the control interface and the liquid source comprising a pump configured to cause a fluid to flow from the reservoir into the at least one lumen in response to the position of the control interface indicated by the sensor.

11. The apparatus of claim 1, wherein the liquid source comprises a condenser configured to extract liquid from an atmosphere and dispense the liquid into the reservoir.

12. The apparatus of claim 1, comprising a gas source configured to pressurize the reservoir in response to operation of the control interface.

13. The apparatus of claim 1, comprising a tower including a video processor wherein an umbilicus couples the handle to the tower and the video processor is coupled to the at least one electrical connection in the handle via the umbilicus.

14. The apparatus of claim 13, wherein the tower includes a gas source configured to pressurize the reservoir in response to operation of the control interface.

15. An apparatus, comprising:
an elongate member comprising at least one lumen;
a handle fixedly coupled to the elongate member, the handle comprising a control interface and a supply port, the control interface operable to control fluid communication between the supply port and the at least one lumen, wherein the handle includes at least one electrical connection to the elongate member; and
a liquid source comprising an adapter and a reservoir removably coupled to the adapter and the adapter removably coupled to the handle via the supply port, wherein the adapter includes threads that the reservoir screws into.

16. An apparatus, comprising:
an elongate member comprising at least one lumen;
a handle fixedly coupled to the elongate member, the handle comprising a control interface and a supply port, the control interface operable to control fluid communication between the supply port and the at least one lumen, wherein the handle includes at least one electrical connection to the elongate member; and a liquid source comprising an adapter and a reservoir removably coupled to the adapter and the adapter removably coupled to the handle via the supply port, wherein the supply port includes threads that the adapter screws into.

\* \* \* \* \*